United States Patent [19]

Miyai et al.

[11] 4,104,584
[45] Aug. 1, 1978

[54] MOISTURE CONTENT METER

[75] Inventors: Yukio Miyai, Osaka; Takeshi Kojo; Junichi Takahashi, both of Kyoto; Satoshi Yoshioka, Nagaokakyo; Kensuke Nakamichi, Ibaraki; Kozo Okada, Osaka; Setsuko Takeda, Muko, all of Japan

[73] Assignee: Matsushita Electric Industrial Co., Ltd., Kadoma, Japan

[21] Appl. No.: 764,864

[22] Filed: Feb. 2, 1977

[30] Foreign Application Priority Data

Feb. 6, 1976 [JP] Japan .................................. 51-12530

[51] Int. Cl.² ........................................... G01R 27/04
[52] U.S. Cl. ............................................... 324/58.5 R
[58] Field of Search ................ 324/58.5 R, 58.5 A, 324/58.5 B, 58.5 C

[56] References Cited

U.S. PATENT DOCUMENTS

| | | | |
|---|---|---|---|
| 2,596,530 | 5/1952 | Clarke | 324/58.5 B |
| 2,630,472 | 3/1953 | McArthur | 324/58.5 C |
| 3,586,971 | 6/1971 | Bosisio | 324/58.5 C |

FOREIGN PATENT DOCUMENTS 1,351,747   5/1974   United Kingdom .............. 324/58.5 A

*Primary Examiner*—Stanley T. Krawczewicz
*Attorney, Agent, or Firm*—Cushman, Darby & Cushman

[57] ABSTRACT

A moisture content meter comprising
  a microwave generator for generating a microwave signal of a constant power level,
  a microstrip transmission line connected in a manner to receive at one end thereof the microwave signal from said microwave generator and disposed in a manner that a flowing sample object, for instance cereal, contacts substantially the surface thereof and
  a microwave detector connected in a manner to detect the remaining power level after absorption by the flowing sample object of the microwave signal taken from the other end of said microstrip transmission line.

4 Claims, 6 Drawing Figures

MOISTURE CONTENT METER

BACKGROUND OF THE INVENTION

This invention relates to a moisture content meter utilizing the microwave absorption phenomenon of water in the sample.

In case of storing cereals, lumber, fabrics, paper, processed foods or the like for a long period, some kind of drying operation to keep the moisture contents in those materials to a certain level suitable for storage is essential for the purpose of preventing deterioration by mold or dampness or of regulating them to processing or storing conditions.

There are two commonplace ways of drying namely: (1) by the solar heat; (2) by a dryer machine. Along with the recent development, however, of farming mechanization such as of cultivators, combines, planting machines, etc., the use of dryers has been making a rapid diffusion in the cereal drying, too.

There are also two principal ways of measuring the moisture contents in cereals in the drying process, namely: (1) firstly measuring the weight of sampled cereals, then drying them by applying infrared rays, and lastly comparing the weights thereof before and after the drying; (2) firstly crushing sampled cereal, then placing it between a pair of electrodes to find the electric resistance value thereof and finding the moisture value with a prepared standard curve. However, since the first method of applying the infrared rays is too expensive, the second method of reckoning from the resistance values has generally been utilized by ordinary farmers. In either case, nevertheless, the measuring largely depends on manual operations while the cereal drying is usually day-and-night operations, thereby requiring day-and-night vigil measuring. Such standard manual operations are apt to cause over-drying or under-drying and resultant deterioration of the quality of cereals. In order to alleviate such strains in the operation and to prevent the risks of over-drying as well as under-drying, it has become an objective to develop an automatic measuring apparatus of moisture contents to be used for drying machines.

There has also been a strong demand for a means to measure moisture contents in flowing or travelling states of some kinds of cereals.

For realizing such demand as mentioned above, utilization of electromagnetic waves, especially microwaves, is effective. This formula is a utilization of the characteristic of microwaves to attenuate when passing through a substance and is based on the principle that the attenuation of microwaves has a certain relation with the moisture amount in the substance.

A typical construction of a microwave-type moisture content meter of prior art is that a pair of horn antennae are connected to a separate microwave oscillator and microwave detector, respectively, are arranged facing each other, and between which a sample object for measuring is placed or moved, its moisture content being measured by the attenuation of microwaves passing through the sample object. In such prior art apparatus, however, for a large amount of, or for bulky sample objects it is impossible to make a direct measurement on the whole object because of heavy attenuation of the microwave. On the other hand, if a measuring of part of the object is attempted, it is necessary to arrange either the horn antenna with the oscillator or the one with the microwave detector in a position buried in the flow of the flowing sample object and hence, not only does the construction of the device become complicated, but also the free flow or transit of the sample object is impeded, thereby reducing the practical value of the apparatus.

Another known method is to measure the moisture contents from the transmission loss of microwaves when the sample object contacts a microwave-guide path. In the case of employing a wave-guide path of such construction, however, it is difficult to control characteristic impedances of the wave-guide path to a target value, and therefore, it is also difficult to form a highly efficient microwave circuit with small reflection by coupling other microwave circuit parts thereto. Therefore, this method has also has a shortcoming that a practical moisture sensor is difficult to achieve.

SUMMARY OF THE INVENTION

The present invention is intended to provide a moisture content meter capable of solving the abovementioned problems, and in particular, of precisely and continuously measuring the moisture contents in flowing or transitive objects such as cereals or the like.

DETAILED DESCRIPTION OF THE INVENTION

Figure 1:
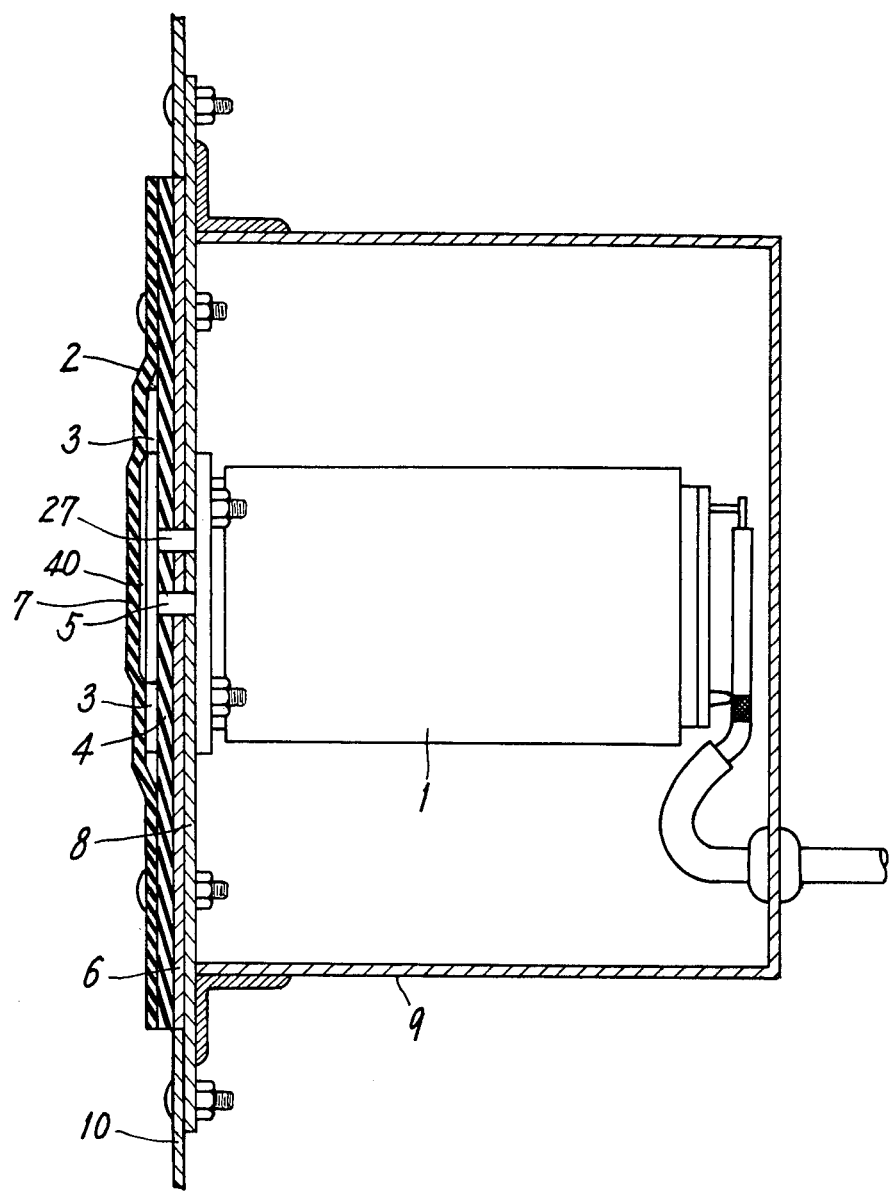
FIG. 1 is a plan view, partially in section of a moisture content meter embodying the present invention.

FIG. 1 is a partially sectional plan view showing one example of apparatus of this invention. This apparatus is constructed as follows:

A ground conductor is formed by coating one face of a dielectric substrate 4 with a metal film 6. A microstrip transmission line 2 is formed by fixing a micro-strip line 3 on the other face of said dielectric substrate 4. All of the abovementioned parts, together with a microstrip transmission line protection film 7 made of dielectric material and with a microstrip transmission line supporting plate 8, are fixed on one end of a protection cylinder 9. And the same end of this protection cylinder 9 is fixed on a wall 10 of a flowing object container (for instance, a wall of a cereal container, in case of a cereal drying machine).

Said microstrip transmission line protection film 7 is not necessarily indispensable for a moisture content measuring device, but it protects the stripline from damage by the flowing object and is very effective for improving reliability of the apparatus. The protection film 7 is located inside the container body, and the flowing object flows partially contacting this protection film 7.

Microwave energy of a constant output power is generated by an oscillator and by an output-controlling circuit, the oscillator and the output-controlling circuit being built in a microwave controlling unit 1, and being fed to a feeding terminal of the micro-strip line 3 by a first coaxial line 27 passing through the dielectric substrate 4. The microwave travels along the micro-strip line 3 and thereafter comes back to the microwave controlling unit 1 via a second coaxial line 5. The microwave power coming back is measured by a detector built in the microwave controlling unit 1.

Transmission loss of the microwave at the micro-strip line 3 varies in acccordance with the moisture content of the flowing obejct if other conditions are the same. Therefore, by measuring the transmission loss, the moisture content can be obtained by referring to a prepared standard curve. In such a device, dielectric loss of the dielectric substrate 4 is desirably small in order to improve the measuring sensitivity of moisture content rate. Furthermore, in case the flowing object is of granular substance like cereals, it is desired to eliminate increased averaging of measuring value by enlarging the area occupied by the micro-strip line 3 making it large enough so as to decrease the variation of measured value due to the difference between loss by air spaces among the granules and loss by the granular substance. A suitable material for the dielectric substrate 4 is a plate of a polytetrafluoroethylene resin impregnated fiber glass. Its practical thickness is 0.2 to 5 mm, the mechanical strength being insufficient if too thin and its cost too much if thicker. Material for the measuring part protection film 7 is desirably to mechanically strong, very durable against abrasion, quite resilient, and low in micro-wave absorption. A polyester film is suitable for such properties for the measuring part protection film. Its appropriate thickness is 50 to 300 μ, it being mechanically not strong enough if too thin and losing sufficient resilience if too thick. For the ground conductor 6 and the microstrip line 3, metals having good electrical conductivity and easy to precisely etch are suitable, e.g., copper, aluminum or gold. In order to reduce the size of the microwave controlling unit 1, microwave integrated circuits (MIC) is employed herein, and hence, the distance between the coaxial lines 5 and 27 becomes small. Accordingly, in order to enlarge the area of the microstrip line 3, as mentioned above, for decreasing the variation of the measured value, it is necessary to arrange the micro-strip line 3 in a loop shape. Furthermore, the width of the microstip line 3 is desirably large, within a range allowable for a matching condition with the microwave circuit including microstrip transmission line 2.

In the present example the microstrip transmission line 2 to satisfy the abovementioned condition was obtained by selecting the width of the micro-strip line 3 in the range of 5 to 20 mm. For the microstrip transmission line supporting plate 8, it is preferably to use materials which have sufficient mechanical strength, a thermal expansion coefficient near that of the dielectric substrate 4 of the microstrip transmission line and a low heat conduction coefficient. An epoxy resin plate of 2 to 10 mm in thickness is used for such a plate.

Figure 2:
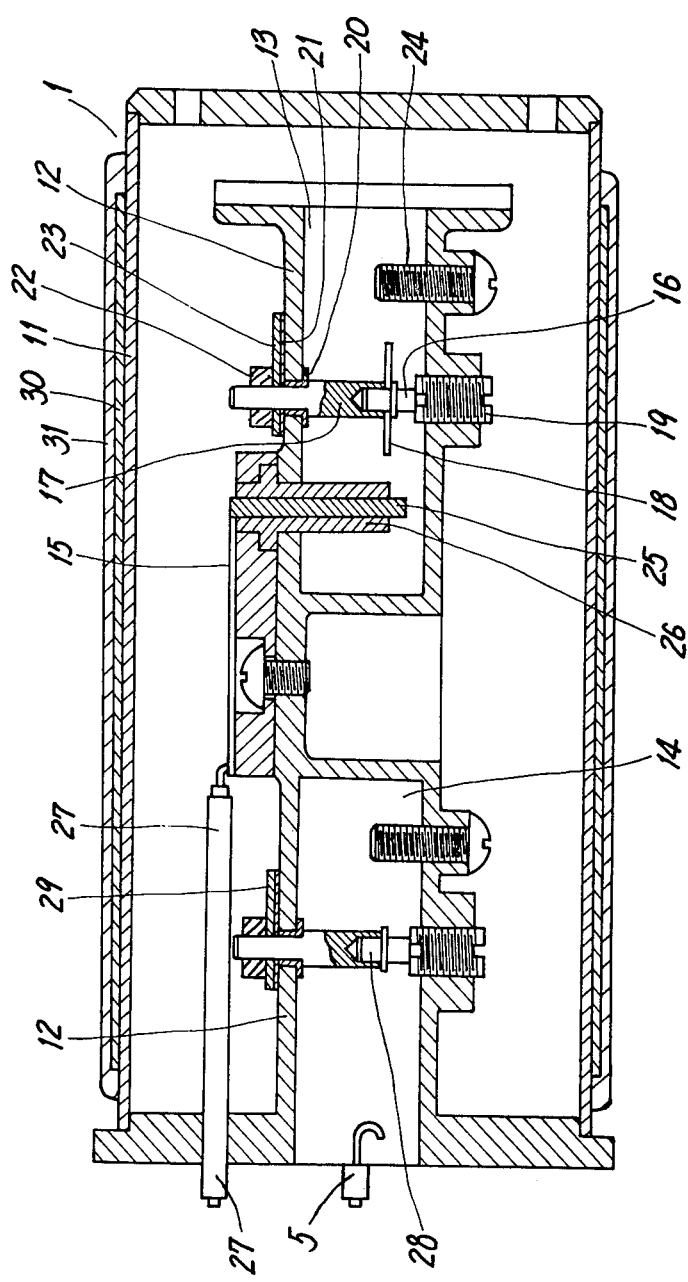
FIG. 2 is a sectional plan view of a microwave controlling unit 1 of the apparatus forming a portion of FIG. 1.

As shown in FIG. 2, the microwave controlling unit 1 comprises a wave-guide structure 12 inside the cylindrical body 11. Said structure 12 comprises a first resonance cavity 13, a second resonance cavity 14 and a microwave integrated circuit 15 formed on a dielectric substrate connected with the first resonance cavity 13 by a coaxial line consisting of a central conductor 25 and a sleeve of the dielectric substance 26.

In the first resonance cavity 13, a solid-state oscillation element 16 for instance, a Gunn diode, is inserted with an oscillation adjusting ring 18 at the tip of a metal conductor post 17 and is fixed between the post 17 and a screwed supporter 19. For the solid-state oscillation element 16, an avalanche diode made of germanium, for example, can be used. The metal conductor post 17 is fixed, in insulated relationship from the cavity wall of the waveguide structure 12, by a screw 22, in a manner such that D.C. input can be supplied to the diode 16. When the D.C. power is supplied to the diode 16 through a metal plate 23 on an insulating thin plate 21 by a wire (not shown in the drawing), leakage of the microwave to the D.C. source is stopped by the insulating thin plate 21 and the metal plate 23 acting as a choke for the resonance cavity. The oscillation characteristic of the microwave can be minutely adjusted by an adjusting stub 24 inserted into the first resonance cavity 13.

The second resonance cavity 14 constitutes a detector. The second cavity has a detector diode 28 and is constructed in the same manner as the first resonance cavity 13 except for the omission of the oscillation adjusting ring 18 therein. For the detector diode 28, a Schottkey barrier diode or a point-contact structure diode, for example, may be employed.

Figure 3:
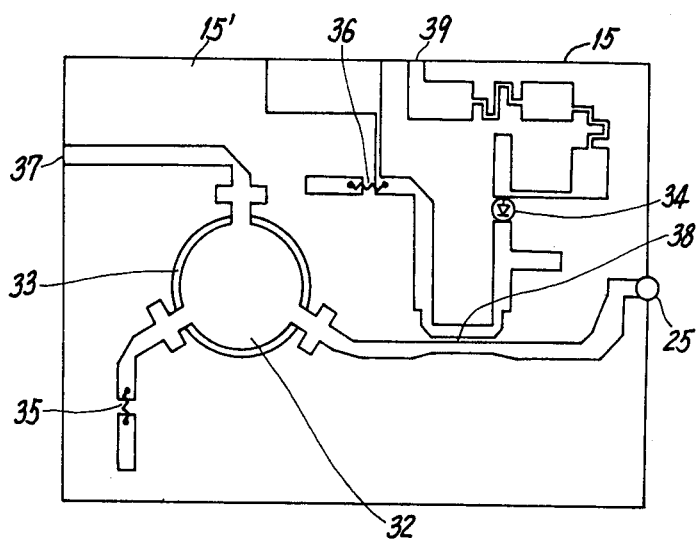
FIG. 3 is a plan view of a microwave integrated circuit 15 included in the microwave controlling unit of FIG. 2.

Microwave integrated circuits 15 comprises a printed circuit substrate with a 2-dimensional conductor pattern of a microwave passive circuit as shown in FIG. 3. The conductors are formed on an alumina ceramic substrate 15' in a desired microstrip pattern by vapor deposition of nichrome and gold utilizing a known photo-etching method. In this passive circuit, a desired opening is formed on the alumina ceramic substrate to form the area of an isolator 32, and a disc 33 of manganese-magnesium ferrite is stuck in the opening an by adhesive. Moreover, a detector diode 34, a resistor 35 with a resistance of 50Ω and a resistor 36 with the same resistance are connected respectively to the strip line at desired positions thereof. In addition, in this integrated circuit structure, a directional coupler 38 is disposed in the pre-stage of the isolator 32. The directional coupler 38 is for leading a part of the microwave signal from the aforementioned first resonance cavity 13 to the detector diode 34 and then feeding the signal detected by the detector diode 34 back to the D.C. power source. With the detected microwave signal, the D.C. input to the solid-state oscillation element 16 is controlled to make the level of the output from the first resonance cavity 13 constant. In the circuit of FIG. 3, the terminal 39 is an output terminal for the detected signal, and the resistors 35 and 36 are the microwave absorbing and terminating resistors, respectively. It is possible to use a simple ferrite plate, instead of the alumina ceramic with the stuck ferrite disc 33, and also to form the strip line by means of printing and firing of a conduction ink.

Furthermore, as shown in FIG. 2, a heater 30 and a heat insulator 31 are disposed on the outer face of the cylindrical body 11, so that the microwave controlling unit 1 is kept at a constant temperature by the heater 30 and a known temperature regulator (not shown) so as to prevent erroneous indication of moisture value due to change of surrounding temperature. Known electric heating by metal wires, metal ribbons, resistor films, etc. can be used for the heater 30.

Figure 4:
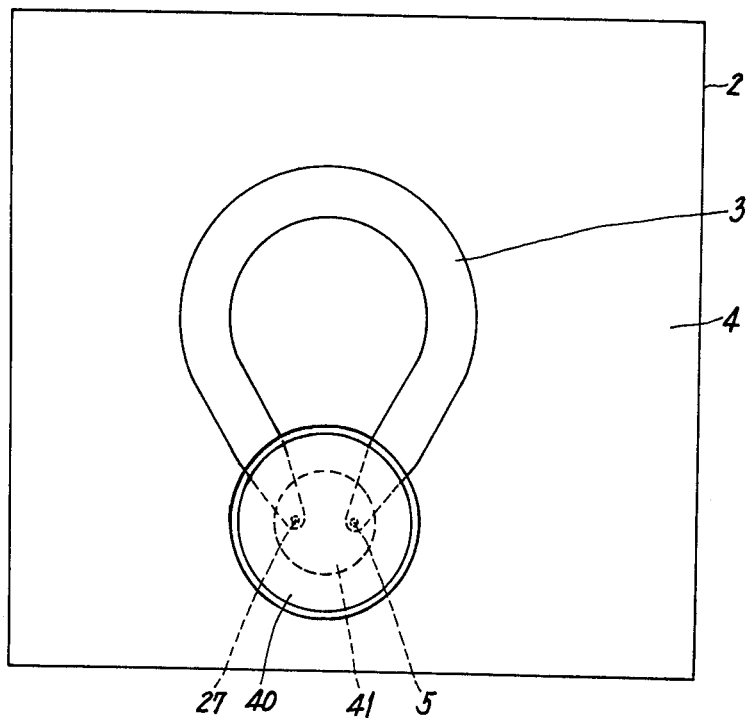
FIG. 4 is a front view of a micro-strip transmission line 2.

The microstrip transmission line 2, as shown in FIG. 4, comprises the dielectric substance 4 and the microstrip line 3 formed by a photo-etching method, etc. on the surface of the dielectric substrate 4. The microstrip transmission line 2 is coated with a protecting film 7. Since the micro-strip transmission line 2 has a high sensitivity, it tends to be too unstable for a moisture sensor. Therefore, the micro-strip line 3 is doubly protected at both ends thereof by a cover 40. The cover 40 is made of a dielectric plate of, for example, 5 mm in thickness and has a recess 41 capable of holding both ends of the micro-strip line 3 on one side thereof. Since the side part of cover 40 tends to impede smooth flow of the sample object by lying in its way, the side part of the cover 40 is preferred to be tapered to decrease such disturbance. As dielectric materials for the cover 40, such materials with small dielectric loss and easily mouldable such as fluorine-contained resin, polyethylene, polypropylene, polystyrol or nylon, can be used.

The operation of the present moisture content meter is described in detail as follows:

First, microwave energy from the first resonance cavity 13 in the microwave controlling unit 1 is led to the microwave integrated circuit 15 through the conductor 25 in the coaxial line. In the microwave integrated circuit, the microwave energy passes through the isolator 32 and is led through the coaxial line 27 from the other end 37 thereof to the micro-strip line 3 in the microstrip transmission line 2. A part of the microwave energy is absorbed by a sample object, for example, a running substance such as a cereal, in the process of passing over the microstrip transmission line 2, since the sample object is substantially contacting the micro-strip line 3 through the protecting film 7. The remainder of microwave energy is transmitted to the abovementioned microwave controlling unit 1 from the output terminal of the micro-strip transmission line 2 through the coaxial line 5. The microwave energy is led to the detector diode 28 in the second resonance cavity 14. The detected D.C. signal from the detector diode 28 is brought to the metal plate 29. When the microwave energy generated by the abovementioned microwave oscillaton element 16 is constant (i.e., when the energy applied to microstrip transmission line 2 is constant), the change of output appearing on the metal plate 29 is a function of the attenuation of the microwave due to absorption by the abovementioned sample object. It is known that, when the sample object is a cereal, the absorption of the microwave exactly corresponds to the moisture content rate of the cereal. Thus, according to the above fact, the moisture content rate of a specific sample object is obtained.

Figure 5:
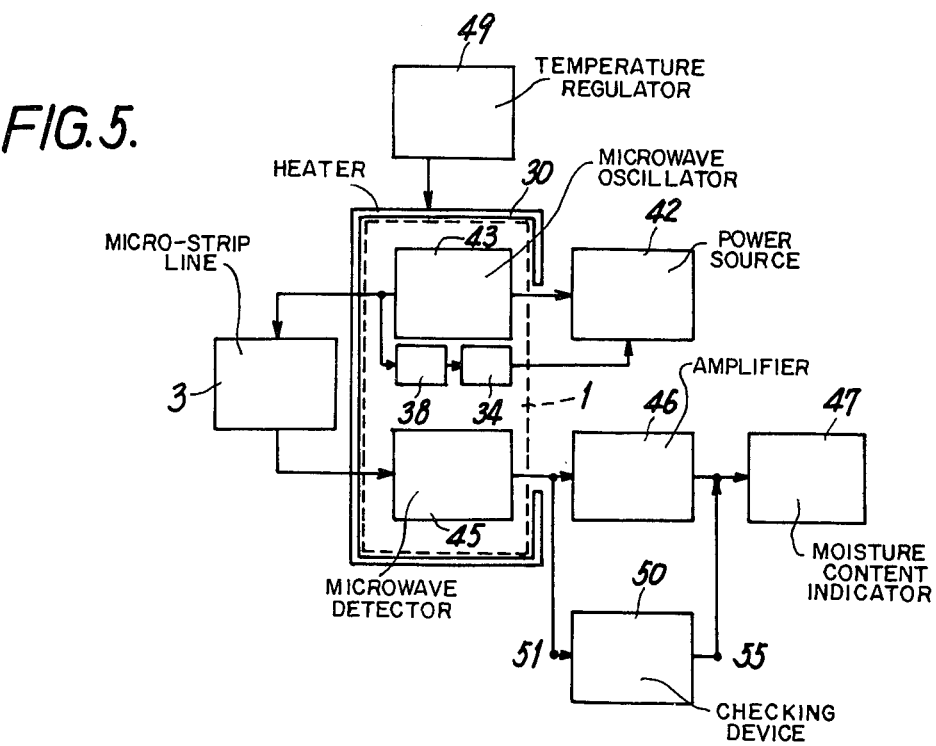
FIG. 5 is a block diagram of the apparatus of FIG. 1.

FIG. 5 is a block diagram of the apparatus of the abovementioned example. The operation of the moisture content meter of this invention is elucidated referring to FIG. 5 as follows:

The microwave oscillator 43 comprising the solid-state oscillation element 16 and the resonance cavity 13 is driven by a stabilized power source 42 and generates a microwave. The microwave is led into the micro-strip transmission line 2 from which a part of the microwave is absorbed by the sample object. The microwave attenuated by the sample object is detected by the microwave detector 45 comprising the solid-state detector diode 28 and the resonance cavity 14, and a D.C. output voltage of the detector diode 28 indicates a signal representative of the moisture value. Then, the D.C. signal is amplified by an amplifier 46 and led to an ammeter acting as a moisture indicator 47. The microwave oscillator 43 and the microwave detector 45 are kept at a constant temperature slightly higher than the highest surrounding temperature, for example, between 25°-65° C, by the heater 30 and a temperature regulator 49. The present moisture content meter is provided with a checking device 50, and therefore, even any layman can easily check whether the moisture content meter is in good working order or not. This is an important practical point.

The principle of the checking device 50 is based on the fact that in case the stabilized D.C. power source 42, the microwave oscillator 43, the micro-strip transmission line 2, the microwave detector 45, the heater 30 and the temperature regulator 49 are normally operating after assembled and adjusted, then, in the absence of the flowing sample object contacting the micro-strip transmission line 2, the microwave detector 45 will indicate a constant D.C. voltage higher than that when a sample object is contacting the micro-strip line 3.

Figure 6:
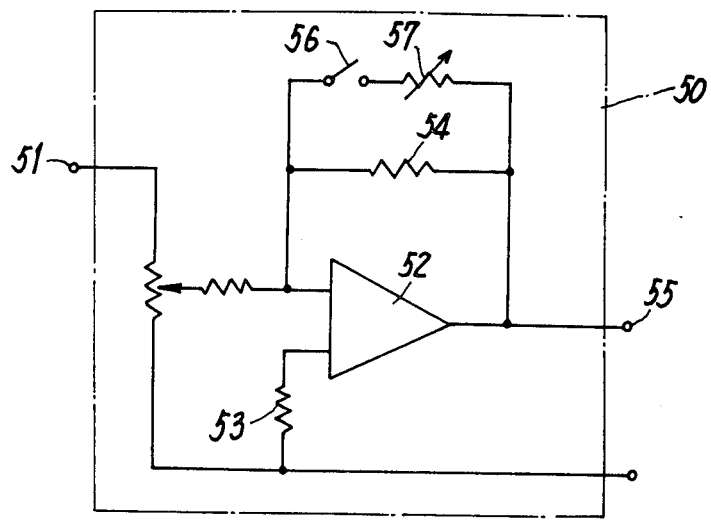
FIG. 6 is a circuit diagram of a checker for the apparatus of the present invention.

An example of the checking device 50 is shown in FIG. 6. The detected voltage is transmitted to an input terminal 51 from the detector 45 and then led into moisture content indicator 47 through an amplifier comprising an operational amplifier 52, resistors 53 and 54 and through an output terminal 55. The checking device 50 comprises a switch 56 and a variable resistor 57. By closing the switch 56, an amplification coefficient of the amplifier 52 is changed by the predetermined degree and the arm of a moisture content indicator 47 points a value marked for calibration of the moisutre content indicator 47. By reading the indication, it can be easily known whether all parts of the moisture content meter except the amplifier 46 are normally operating or not. Since the amplifier 46 comprises low frequency circuits, it has much higher stability than the microwave circuit and therefore, through the adoption of said checking device 50, the moisture content meter can adequately function.

The microwave controlling unit 1 in FIGS. 1 and 2 need not necessarily be constructed in a combined body consisting of the microwave generator and the detector. Furthermore, the microwave circuit including the microwave controlling unit 1 and the microstrip transmission line 2 can be constructed in a combined body together with the stabilized power source 42, the amplifier 46, the moisture content indicator 47, etc. in a protective case.

As explained above, in the moisture content meter of the present invention, the microwave oscillator and the detector are joined by the microstrip transmission line which includes a micro-strip line. To measure the moisture content of the sample object, the sample object is made contact or flow along the micro-strip line either directly or over the protection film thereon. In this way, the moisutre content rate of the sample object can be measured instantaneously and continuously. Moreover, in case the microwave oscillator and the microwave detector are formed into a combined body using the microwave integrated circuit, the apparatus is made compact. Furthermore, by employing the method of measurement of the moisture by contacting the micro-strip line instead of transmitting the microwave across the sample object, the microwave does not attenuate so much even when measuring a bulky object. A very bulky sample object can be measured by measuring only a part of the sample object using the present moisture content meter.

Furthermore, since a flat micro-strip line is used as the element to be placed near the sample object, even if mounted on a drying-storing apparatus for cereals, etc., the present apparatus will not deteriorate the function and appearance of such drying-storing apparatus. Moreover, by mounting on the drying-storing apparatus, the present moisture content meter can be used in an automatic controlling means to maintain constant the moisture content rate of cereals stored in the drying-storing apparatus, by additionally providing an automatic alarm for signaling completion of a preset drying of the sample object. In such manner, work can be alleviated and over-drying or under-drying can be prevented. Additionally, all operations of drying cereals, measuring moisture contents thereof and storing them can be completely automated by providing the drying-storing apparatus with a device of applying the measured signal to an operation circuit of such drying-storing apparatus.

What is claimed is:

1. A moisture content meter comprising
   a microwave generator for generating a microwave signal of a constant power level,
   a microstrip transmission line connected in a manner to receive at one end thereof the microwave signal from said microwave generator and disposed on one side of a sample body to be measured so as to substantially contact the surface thereof and
   a microwave detector connected in a manner to detect the power level of the microwave signal taken out from the other end of said microstrip transmission line, the difference in power lines at the opposite ends of the microstrip reflecting the moisture content of the body.

2. A moisture content meter of claim 1, wherein said microstrip transmission line has a loop-shaped pattern having a developed length sufficiently longer than the distance between said one end and said other end of said microstrip transmission line.

3. A moisture content meter of claim 1 wherein the surface of said microstrip transmission line has a protection film of insulating substance.

4. A moisture measuring apparatus of claim 1 which further comprises microwave integrated circuits for controlling the oscillation power level of the microwave signal to be constant.

* * * * *